United States Patent
Hochstrasser et al.

(10) Patent No.: US 7,368,247 B2
(45) Date of Patent: May 6, 2008

(54) DIAGNOSTIC ASSAY FOR TRANSMISSIBLE SPONGIFORM ENCEPHALOPATHIES

(75) Inventors: Denis Francois Hochstrasser, Geneva (CH); Jean-Charles Sanchez, Geneva (CH); Catherine Gabrielle Zimmermann, Geneva (CH); Elisabeth Guillaume, Annemasse (FR)

(73) Assignee: Universite De Geneve, Geneva (CH)

( * ) Notice: Subject to any disclaimer, the term of this patent is extended or adjusted under 35 U.S.C. 154(b) by 30 days.

(21) Appl. No.: 10/238,557

(22) Filed: Sep. 10, 2002

(65) Prior Publication Data

US 2003/0157580 A1  Aug. 21, 2003

Related U.S. Application Data

(63) Continuation of application No. PCT/EP01/02894, filed on Mar. 12, 2001.

(30) Foreign Application Priority Data

Mar. 10, 2000 (GB) ................................. 0005683.8
Mar. 14, 2000 (GB) ................................. 0006064.0

(51) Int. Cl.
*G01N 33/53* (2006.01)

(52) U.S. Cl. .......................... 435/7.1; 435/6; 435/7.92; 435/7.94; 436/16; 436/501; 436/517; 436/548; 436/811; 436/819; 530/359

(58) Field of Classification Search .................... 435/6, 435/7.1, 7.92, 7.93, 7.94; 436/501, 506, 436/512, 517, 548, 811, 819, 16; 530/359
See application file for complete search history.

(56) References Cited

FOREIGN PATENT DOCUMENTS

| | | |
|---|---|---|
| EP | 0 861 900 | 9/1998 |
| FR | 2 763 692 | 11/1998 |
| WO | WO 98/23962 | 6/1998 |
| WO | WO 98/45440 | 10/1998 |
| WO | WO 99/04237 | 1/1999 |

OTHER PUBLICATIONS

Strongin, Sensitivity, Specificity, and Predictive Value of Diagnostic Tests: Definitions and Clinical Applications, Laboratory Diagnosis of Viral Infections, Lennette, E., ed., Marcel Dekker Inc., New York, pp. 211-219 (1993).*

Pu et al. "Expression of fatty acid binding proteins is altered in aged mouse brain," Mol Cell Biochem, 1999, 198:69-78.

(Continued)

*Primary Examiner*—Gailene Rio Gabel
(74) *Attorney, Agent, or Firm*—Arent Fox LLP

(57) ABSTRACT

Heart and brain fatty acid binding proteins (H-FABP, B-FABP) are markers for TSEs, especially CJD. The invention provides a diagnostic assay for either of these markers, preferably by enzyme immunoassay using a specific antibody thereto. Since H-FABP is also a marker for acute myocardial infarction (AMI), to distinguish CJD from AMI requires an assay specific to AMI, e.g. using troponin-1 or CK-MB as a marker, also to be carried out.

9 Claims, 1 Drawing Sheet

OTHER PUBLICATIONS

Ohkaru et al., "Development of a sandwich enzyme-linked immunosorbent assay for the determination of human heart type fatty acid-binding protein in plasma and urine by using two different monoclonal antibodies specific for human heart fatty acid-binding protein," 1995, Journal of Immunological Methods, 178:99-111.

Meyers-Payne et al. "Isolation and Characterization of Two Fatty Acid Binding Proteins from Mouse Brain", Journal of Neurochemistry, 1996, 1648-1656.

Gorski et al., Increased Fatty Acid-Binding Protein Concentration In Plasma of Patients with Chronic Renal Failure, Depts. of Physiol and Nephrol, 193-195.

Myers-Payne, S., et al., Isolation and Characterization of Two Fatty Acid Binding Proteins from Mouse Brain, 1996, , *Journal of Neurochemistry*, 1648-1656.

Godbout, R. et al., Correlation of B-FABP and GFAP Expression in Malignant Glioma, 1998, *Oncogene*, 1955-1962.

Kurtz, A. et al., The Expression Pattern of a Novel Gene Encoding Brain-fatty Acit Binding Protein Correlates With Neuronal and Glial Cell Development, 1994, *The Company of Biologists Limited*, 2637-2649.

* cited by examiner

DIAGNOSTIC ASSAY FOR TRANSMISSIBLE SPONGIFORM ENCEPHALOPATHIES

This application is a continuation application of International Patent Application No. PCT/EP01/02894, filed Mar. 12, 2001 and published on Sep. 13, 2001, as WO 01/67108, which claims priority to British application No. 0006064.0, filed Mar. 14, 2000, which claims priority to British application No. 0005683.8, filed Mar. 10, 2000.

BACKGROUND OF THE INVENTION

1. Field of the Invention

This invention is in the field of diagnostic assay using a protein or an antibody thereto.

2. Description of the Related Art

Transmissible spongiform encephalopathies (TSEs) are neurodegenerative diseases of the central nervous system. They can be transmitted, inherited or occur sporadically and are observed in animals, e.g. as bovine spongiform encephalopathy (BSE) in cattle or scrapie in sheep, as well as in humans as Creutzfeldt-Jakob disease (CJD), Gerstman Straussler Scheinker syndrome, Fatal Familial Insomnia or Kuru. They have a long incubation period, leading to ataxia, dementia, psychiatric disturbances and death. Neuropathological changes include vacuolar degeneration of brain tissue, astrogliosis and amyloid plaque formation. The diseases are difficult to diagnose pre-mortem.

The cerebrospinal fluid (CSF) of CJD patients displays two additional polypeptide by two-dimensional polyacrylamide gel electrophoresis [Harrington, M. G. New England Journal of Medicine 315, 279 (1986), Hsich, G., Kenney, K., Gibbs, C. J., Lee, K. H. & Harrington, M. B. New England Journal of Medicine 335, 924 (1996).] The function of these 14-3-3 polypeptides remain unclear in TSE. They can be used in a pre-mortem test for CJD diagnostic evaluation, but have low specificity.

Monoclonal antibodies to the abnormal form of prion protein are available and can be used in an enzyme-linked immunoassay, as described in PCT Specifications WO 98/23962 and 98/32710 and Schmerr, M. J., the Beckman Coulter Pace Setter Newsletter 3(2),1-4 (June 1999), but these procedures have not yet been fully developed.

Development of new non-invasive blood CAD and BSE markers would help clinicians to establish early diagnosis.

SUMMARY OF THE INVENTION

It has now surprisingly been found that two fatty acid binding proteins (FABP), known as heart (H-FABP) and brain (B-FABP), are markers for TSEs. Thus, the invention provides a diagnostic assay for a TSE or the possibility thereof in a sample of body fluid taken from a subject suspected of suffering from the TSE, which comprises determining the concentration of heart or brain fatty acid binding protein (H-FABP or B-FABP) in the sample. The method is especially applicable to the diagnosis of CJD, especially new variant CJD, in human patients, and to BSE in ruminant animals such as cattle.

Conveniently the method is carried out using an antibody to H-FABP or B-FABP, whereby the extent of the reaction between the antibody and the FABP in the sample is assayed and related to the concentration of FABP in the sample. The concentration thus determined is used to make or assist in making a diagnosis.

The present invention enables an assay of high sensitivity, specificity and predictive accuracy for CJD to be carried out.

"Sensitivity" is defined as the percentage of true positives given by the assay on samples taken from patients in whom clinical examination has confirmed CJD. "Specificity" means the percentage of true negatives given by the assay on control samples, i.e. from patients in whom clinical examination has not revealed CJD. "Predictive accuracy" means the ratio of true positives to total positives (true+false) expressed as a percentage.

H-FABP is a known marker of acute myocardial infarction (AMI), see Ishii, J. et al., "Serum concentrations of myoglobin Vs human heart-type cytoplasmic fatty-acid binding protein in early detection of acute myocardial infarction", Clinical Chemistry 1997;43 1372-1378. Therefore, in order to use an assay for H-FABP for the diagnosis of CJD in humans to better advantage, it is desirable to perform another kind of assay for AMI (one in which the marker is not a FABP) in order to eliminate from the diagnosis for CJD those patients who are positive in the AMI assay.

Thus, in a particular embodiment, the invention provides a method which comprises determining the concentration of H-FABP in a first assay, as defined above, whereby a positive result indicates either a CJD or acute myocardial infarction, and which further comprises carrying out a second diagnostic assay, for acute myocardial infarction (AMI) only, whereby a positive result in the H-FABP assay and a negative result in the assay for AMI indicates that the patient might be suffering from CJD. Assays using Troponin-I and Creatine Kinase-MB (CK-MB) as early biochemical markers of acute myocardial infarction (AMI) are well known and suitable for the above purpose.

A similar H-FABP and also a brain-specific fatty acid binding protein (B-FABP) have been found in the brain of mice, see Pu, L. et al., Molecular and Cellular Biochemistry 198, 69-78 (1999). Brain H-FABP (not to be confused with B-FABP) is believed to differ from heart H-FABP by a single amino acid substitution. However, B-FABP differs considerably. Sellner, P. A. et al., "Development role of fatty acid binding proteins in mouse brain" Dev. Brain Res. 89, 33-46 (1995), estimated the DNA homology at 69%, while A. Schreiber et al., "Recombinant human heart-type fatty acid binding protein as standard in immunochemical assays", Clin. Chem. Lab. Mod. 36(5), 283-288 (1998), mention 0.64% amino acid sequence homology and that a monoclonal antibody to human H-FABP is cross-reactive with human B-FABP to the extent of only 1.7%.

Now that the present inventors have found that H-FABP is a marker for CJD, it is a very reasonable prediction that B-FABP will also be. Since B-FABP is specific to brain tissue and does not appear to react significantly with a monoclonal antibody to H-FABP, it will not give positives for AMI, making a separate assay for AMI unnecessary.

DESCRIPTION OF PREFERRED EMBODIMENTS

Figure 1:
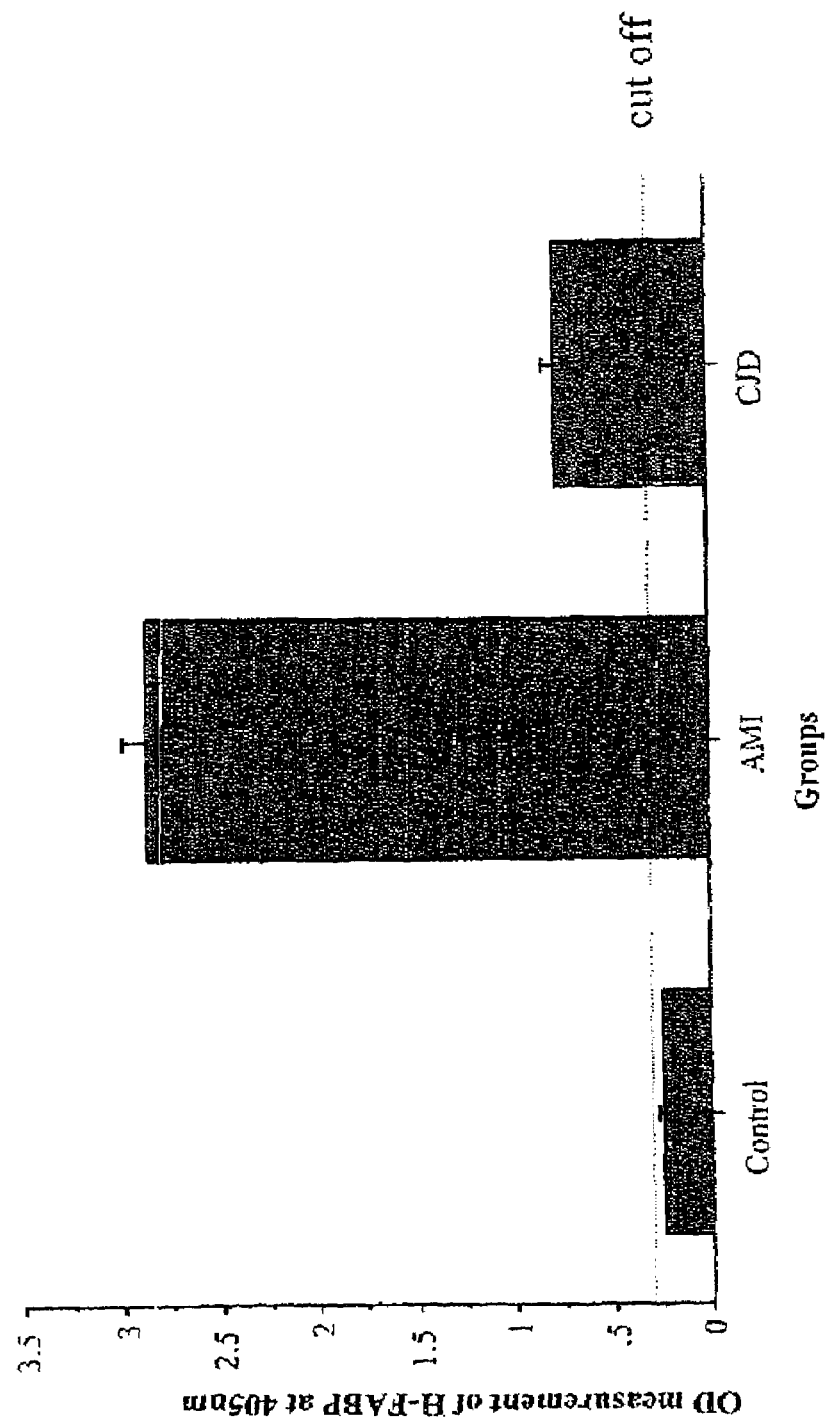
FIG. 1 shows a graphic representation on the y-axis of H-FABP concentration represented by optical density measurement at 405 nm, as determined by the method of the invention, for (a) a control group having neither CJD nor AMI (b) a group having AMI and (c) a group having CJD.

For the method of assay, the sample can be taken from any convenient body fluid of the subject, but preferably plasma or serum (rather than whole blood). Cerebrospinal fluid (CSF) is another useful fluid, particularly when testing animals such as cattle.

The method is considered applicable to all types of TSE, including those referred to above, and to any human or animal suffering or suspected of suffering therefrom. Particularly, the invention is applicable to all types of CJD in humans, including new variant, sporadic and genetic (familial). Further, it is applicable to BSE in cattle and BSE-like disease in other animals, e.g. deer.

The marker, H-FABP or B-FABP, is preferably measured by an immunoassay, using a specific antibody to H-FABP and measuring the extent of the antigen (H-FABP or B-FABP)/antibody interaction. For the diagnosis of human patients, the antibody is preferably anti-human H-FABP or B-FABP. Similarly, if the subject is an animal the antibody is preferably anti- to the H-FABP or B-FABP of the same animal variety, e.g. anti-bovine H-FABP or B-FABP if the patient is bovine. However, there is some cross reactivity of the antibodies between species, often enabling a heterologous antibody to be used: for example anti-rat/mouse H-FABP can be used to detect BSE in cattle. It may be a monoclonal antibody (conveniently mouse) or an engineered antibody. Preferably a mouse anti-human, anti-bovine etc. monoclonal antibody is used. Antibodies to H-FABP are known, e.g. 66E2 and 67D3 described by Roos, W. et al., "Monoclonal antibodies to human heart type fatty acid-binding protein", J. Immunol. Methods 183 149-153 (1995). Antibody 66E2 is commercially available. Also, the usual Köhler-Milstein method may be used to raise H-FABP or B-FABP antibodies. The source of protein for this purpose can be the naturally derived or recombinant DNA-prepared protein. Recombinant human H-FABP and B-FABP have been described by Schreiber, A. supra and Shimizu, F. et al., "Isolation and expression of a cDNA for human brain fatty acid binding protein (B-FABP)", Biochim Biophys. Acta 1354, 24-28 (1997), respectively. Less preferably, the antibody may be polyclonal.

Any known method of immunoassay may be used. A sandwich assay is preferred. In this method, a first antibody to the FABP is bound to the solid phase such as a well of a plastics microtitre plate, and incubated with the sample and with a labelled second antibody specific to the H-FABP or B-FABP to be detected. Alternatively, an antibody capture assay could be used here, the test sample is allowed to bind to a solid phase, and the anti-FABP antibody is then added and allowed to bind. After washing away unbound material, the presence or amount of antibody bound to the solid phase is determined using a labelled second antibody, anti- to the first.

In another embodiment, a competition assay could be performed between the sample and a labelled FABP or a peptide derived therefrom, these two antigens being in competition for a limited amount of anti-FABP antibody bound to a solid support. The labelled FABP or peptide could be pre-incubated with the antibody on the solid phase, whereby the FABP in the sample displaces part of the FABP or peptide thereof bound to the antibody.

In yet another embodiment, the two antigens are allowed to compete in a single co-incubation with the antibody. After removal of unbound antigen from the support by washing, the amount of label attached to the support is determined and the amount of protein in the sample is measured by reference to standard titration curves established previously.

The label is preferably an enzyme. The substrate for the enzyme may be colour-forming, fluorescent or chemiluminescent.

It is highly preferable to use an amplified form of assay, whereby an enhanced "signal" is produced from a relatively low level of protein to be detected. One particular form of amplified immunoassay is enhanced chemiluminescent (ECL) assay. Here, the antibody is preferably labelled with horseradish peroxidase, which participates in a chemiluminescent reaction with luminol, a peroxide substrate and a compound which enhances the intensity and duration of the emitted light, typically 4-iodophenol or 4-hydroxycinnamic acid.

Another preferred form of amplified immunoassay is immuno-PCR. In this technique, the antibody is covalently linked to a molecule of arbitrary DNA comprising PCR primers, whereby the DNA with the antibody attached to it is amplified by the polymerase chain reaction. See Hendrickson, E. R. at al., Nucleic Acids Research 23, 522-529 (1995) or Sano, T. et al., in "Molecular Biology and Biotechnology" ed. Robert A. Meyers, VCH Publishers, Inc. (1995), pages 458-460. The signal is read out as before.

In a particularly preferred procedure, an enzyme-linked immunosorbent assay (ELISA) was developed to detect H-FABP in serum. Since H-FABP is a marker for AMI as well, Troponin-I or CK-MB levels were assayed in order to exclude any heart damage. As described in the Example, these assays were assessed in serial plasma and CSF samples, from patients lacking AMI and CJD, patients with AMI, patients with dementia and patients with confirmed CJD through autopsy. The sensitivity, specificity and predictive accuracy for H-FABP in CJD above a suitable cut-off level were all 100%. Thus, H-FABP detection combined with the Troponin-I or CK-MB assay provides a useful serum marker of CJD diagnosis or brain damage.

The use of a rapid microparticle-enhanced turbidimetric immunoassay, developed for H-FABP in the case of AMI, Robers, M. et al., "Development of a rapid microparticle-enhanced turbidimetric immunoassay for plasma fatty acid-binding protein, an early marker of acute myocardial infarction", Clin. Chem. 44, 1564-1567 (1998), should drastically decrease the time of the assay. Thus, the full automation in a widely used clinical chemistry analyser such as the "COBAS" MIRA Plus system from Hoffmann-La Roche or the "AXSYM" system from Abbott laboratories should be possible and applied for routine clinical diagnosis of CJD.

The H-FABP or B-FABP can be measured by other means than immunoassay. For example, the sample can be subjected to 1 or 2-DE gel electrophoresis and the amount of the FABP estimated by donsitometric scanning of the gel or of a blot therefrom.

The assay of the invention can be used together with one or more other pre-mortem assays for the TSE, including specifically those assays described above. Such combined procedures are particularly useful in diagnosing BSE in ruminant animals such as cattle.

The following Examples illustrate the invention.

EXAMPLE 1

Materials and Methods

Patients

The study population consisted of 3 age-and-gender matched control patients (Control group), 3 confirmed AMI patients (AMI group), 3 confirmed dementia patients (dementia group) and 3 confirmed CJD patients (CJD group). The Control group included 2 men, mean age 66, range 46-86 years, and 1 woman, age 63 years. The AMI group included 2 men, mean age 65, range 40-90 years, and 1 woman, age 72 years. The dementia group included 2 men, mean age 65, range 43-87 years, and 1 women, age 64 years.

The CJD group included 2 men, mean age 68, range 62-74 years, and 1 woman, age 65. Blood and CSF samples were collected for each patient of the CJD. Blood samples were collected in dry heparin-containing tubes. After centrifugation at 1500 g for 15 min at 4° C., tubes were stored at −20° C. until analysis. Patients from the CJD group underwent serial clinical evaluations by neurologists in order to confirm COD diagnosis-Patients from the AMI group were admitted to the hospital with a confirmed AMI (Troponin-I concentration >2 ng/ml). A clinical evaluation was performed on all the patients from the control group to exclude CJD and AMI.

Measurement of Brain and Heart H-FABP

H-FABP levels were measured in plasma by a sandwich ELISA. A 96-well polystyrene microplate (NUNC) was coated with 100 microlitres/well goat anti-human FABP, detecting all isoforms (Spectral Diagnosis HC, Ontario, USA), 20 micrograms/ml in carbonate buffer 0.1M pH 9.6, overnight at 4° C. the plate was automatically washed with PBS (15 mM $Na_2PO_4$-120 mM NaCl-2.7 mM KCl pH 7.4, Sigma) on a BioRad NOVAPATH™ washer. Every washing step was performed with fresh PBS. Non-specific binding sites were blocked with 200 microlitres/well 2% casein in carbonate buffer for 2 h at 37° C. After the washing step, the samples were pipetted in duplicate at 100 microlitres/well. The plate was incubated 2 h at 37° C. After the washing step, 100 microlitres/well of mouse anti-human Heart FABP (clone 66E2, HyCult Biotechnology BV, Uden, Netherlands), 0.3 microgram/ml in PBS-1% BSA, were incubated for 1 h at room temperature (R.T) with shaking. After the washing step, 100 microlitres/well of alkaline phosphatase-labelled anti-mouse immunoglobulin (Dako, Denmark), 1.5 mg/ml in PBS, were incubated 1 h 30 min at room temperature with shaking. After the washing step, 50 microlitres/well of alkaline phosphatase substrate, viz. 1.5 mg/ml paranitrophenylphosphate in diethanolamine, was added and the samples were then incubated for 30 min. The reaction was stopped with 100 microlitres/well IM WaOH. Colour development was measured with a microplate reader at a wavelength of 405 nm.

"Blank" assays in buffer were also performed.

CK-MB and Troponin-I Measurement

AMI was diagnosed by clinical evaluation and Troponin-I and CK-MB measurements. Samples were centrifuged at 1500 g for 15 min, and stored at −20° C. Serum CK-MB and Troponin-I levels were determined using a fluorescent microparticle enzyme immunoassay (MEIA) with an automated chemical analyser "AxSYM" system (Abbott Laboratories, Abbott Park, Ill., USA). The rate of formation of fluorescent products was directly proportional to the amount of Troponin-I in the sample. The detection limit for Troponin-I was 0.3 micrograms/l. CK-MB measurement is proportional to the amount of fluorescent probes and the detection limit was 0.7 micrograms/l.

Statistical Analysis

H-FABP levels were expressed in optical densitometry (OD) values either as mean plus or minus SD or as median and inter-quartile range. Troponin-I and CK-MB levels were expressed in concentration units (ng/ml). The non-parametric Mann-Whitney U-test and Kruskal-Wallis H-test were used to compare H-FABP, Troponin-I and CK-MB concentrations in plasma between groups. "PRISM" software was used to elaborate box/whisker and scatter plots. The 95% confidence intervals (CI) and Receiver Operating Characteristic (ROC) curves, defined by "Analyse-it" software for Microsoft "EXCEL", were used to assess the discriminatory time point of the indicators. See Murphy, J. M. et al., "Performance of screening and diagnostic tests", Arch. Gen. Psychiatry 44, 550-555 (1987). $P<0.05$ was considered statistically significant.

Results

Clinical Characteristics

Patients from the CJD group were given a complete clinical evaluation. CJD was finally diagnosed with the help of brain immuno-histology after autopsy. Patients from the Control group were admitted to hospital and CJD and AMI were excluded by clinical evaluation.

Patients from the AMI group were admitted to the hospital with confirmed AMI with high Troponin-I levels (>2 ng/ml).

Assay results are shown in Table 1 below.

TABLE 1

| Assay type | Control Group plasma | AMI Group plasma | Dementia Group CSF | CJD Group plasma | CJD Group CSF |
|---|---|---|---|---|---|
| H-FABP | | | | | |
| median (25-75%) OD, 405 nm | 0.25 (0.23-0.27) | 2.89 (2.70-3.0) | 0.20 (0.16-0.31) | 0.79 (0.74-0.86) | 0.46 (0.38-0.54) |
| Troponin-1 | | | | | |
| median (25-75%) IU ng/ml | 0 (0.0-0.0) | 50 (50-359) | 0 (0.0-0.2) | 0 (0.0-0.2) | 0 (0.0-0.2) |

H-FABP plasma levels (OD measurement) in the AMI group were significantly higher than the respective level in the Control group (Table 2). The AMI group had a H-FABP median level (range 25-75%) of 2.89 (2.70-3.0) while the Control group had a level of 0.25 (0.23-0.27). The H-FABP plasma level in the CJD group was between the slopes of the AMI and the Control groups. H-FABP median (range 25-75%) level in the plasma CJD group was 0.79 (0.74-0.86). The sensitivity, specificity, and predictive accuracy of B-FABP levels beyond the cut off value of 0.30 were 100%, 100% and 100% respectively. To confirm differences in H-FABP concentrations between AMI and Control groups, Troponin-I was assayed. In addition, in order to discriminate AMI and CJD, they were also assayed on CJD samples. The Troponin-I concentration was measured in each group. Troponin-I concentration in the AMI group was significantly ($p>0.01$) higher than in the Control group.

Discussion

The above results indicate that H-FABP is a potential marker for CJD diagnosis. Since H-FABP was presented as a marker of acute myocardial infarction a few years ago, CJD and AMI had to be discriminated by another AMI biochemical marker such as Troponin-I or CK-MB. After the discrimination of AMI for CJD patient, the serum as well as the CSF H-FABP concentration could be used as a specific marker of CJD.

In the present study, H-FABP assay allowed a sensitivity, a specificity and a predictive accuracy (OD response>0.30) of 100%. These values were significantly higher than those obtained in another method of pre-mortem detection of CJD, which makes use of the protein 14-3-3, a dimeric phosphoserine-binding protein. This method involves immunoblotting with anti-14-3-3 antibody. protein. The three dementia patients were positive to anti-14-3-3 immunoblotting. The specificity of 14-3-3 is not limited to CJD but includes also Alzheimer's dementia, cerebral complications from head injury and some other forms of dementia.

Acute myocardial infarction is diagnosed with the help of biochemical marker assays such as cardiac Troponin-I, Creatine-Kinase MB, myoglobin and recently H-FABP assay. The H-FABP level for CJD could interfere with AMI and discrimination between AMI and CJD was made with the use of other AMI markers.

EXAMPLE 2

Samples of plasma or CSF were taken from human patients. The disease from which the patients were suffering was in some cases clearly CJD, either sporadic (sp) or new variant (v), as determined by autopsy. In other cases ("not CJD ?"), the patient has been diagnosed as not having CJD, but since some of these patients are still alive, this has not necessarily been confirmed by autopsy. The samples were assayed for CJD by the anti-14-3-3 method of the prior art and by the present invention.

The anti-14-3-3 immunoblot was carried out by running the samples on a 12% SDS-PAGE gel in tris-SDS-glycine buffer. The proteins were thereafter transferred by semi-dry electroblotting at a constant 200 mA for 3 hours, in CAPS buffer, onto a PVDF membrane. The membrane was blocked, incubated with an anti-14-3-3 polyclonal rabbit IgG antibody from Santa Cruz, Inc-(Cat sc 629, Lot L117), washed with buffer and incubated with the second antibody, a goat anti-rabbit immunoglobulin labelled with horseradish peroxidase (Dako, Denmark). The membrane was then washed again. The washing after each incubation was done in PBS buffer, pH 7.2, with 5% "Tween" three times quickly and five times for five minutes each time. The peroxidase was then assayed by a standard enhanced chemiluminescence method, using a Boehringer Mannheim kit, "BM Chemiluminescence Blotting Substrate (POD)". The luminescence observed denoted a positive result in the immunoblotting.

The method of the present invention was as described in Example 1, except that the sensitivity cut-off applied (using ROC curves) was at OD>0.2 for plasma samples and OD>0.1 for CSF samples. Table 2 shows the results.

Referring to Table 2, the anti-14-3-3 test was performed twice, by different operatives in the inventors' laboratory, yielding the same results. The correlation between the anti-14-3-3 and the anti-H-FABP results was nearly 100%, the exception being the sample CSF-10, where the result was not clear. The plasma samples gave positives with anti-H-FABP in tour cases in which the anti-14-3-3 test gave a negative. This could mean that the anti-14-3-3 test is not giving a true result in all cases.

TABLE 2

| Sample Designation | Disease Assignment | Anti-14-3-3 Immunoblot (Prior art)* | Anti-H-FABP ELISA (This inv.) |
| --- | --- | --- | --- |
| PLAS2 | vCJD | Negative | Positive |
| PLAS3 | vCJD | Negative | Negative |
| PLAS4 | vCJD | Negative | Positive |
| PLAS5 | spCJD | Positive | Positive |
| PLAS6 | spCJD | Negative | Negative |
| PLAS7 | spCJD | Positive | Positive |
| PLAS9 | not CJD? | Positive | Positive |
| PLAS10 | not CJD? | Positive | Positive |
| PLAS11 | not CJD? | Negative | Positive |
| PLAS12 | not CJD? | Negative | Positive |
| CSF1 | spCJD | Positive | Positive |

TABLE 2-continued

| Sample Designation | Disease Assignment | Anti-14-3-3 Immunoblot (Prior art)* | Anti-H-FABP ELISA (This inv.) |
| --- | --- | --- | --- |
| CSF2 | spCJD | Positive | Positive |
| CSF3 | spCJD | Positive | Positive |
| CSF4 | spCJD | Positive | Positive |
| CSF5 | spCJD | Positive | Positive |
| CSF10 | vCJD | Positive | Positive |
| CSF11 | vCJD | Positive | Unclear |
| CSF12 | vCJD | Positive | Positive |
| CSF6 | not CJD? | Negative | Negative |
| CSF7 | not CJD? | Positive | Positive |
| CSF8 | not CJD? | Negative | Negative |
| CSF9 | not CJD? | Negative | Negative |
| CSF13 | not CJD? | Negative | Negative |
| CSF14 | not CJD? | Negative | Negative |

*Performed twice, by different workers, with the same results.

EXAMPLE 3

The method of the invention was carried out on pooled, concentrated, samples of CSF from 4 cattle diagnosed as having BSE and on pooled, concentrated samples from 3 healthy cattle as controls. (The samples were concentrated with "Microcon",from Amicon, in order to increase the signal to background ratio).

A rat/mouse H-FABP ELISA kit from Hycult Biotechnology B.V., Uden, The Netherlands, was used, according to the manufacturer's instructions, the assay being similar in principle to the sandwich ELISA described in Example 1. However, the first antibody, bound to the wells, was anti-rat/mouse H-FABP, rather than anti-human H-FABP, and the second antibody was peroxidase-labelled, anti-rat/mouse. (These antibodies appear to be anti- to both rat and mouse. It should be explained that this kit was not intended to detect bovine H-FABP. It was found unexpectedly in the present invention that the anti-rat/mouse H-FABP antibody recognises bovine H-FABP). The assay is calorimetric, using SMP substrate and with readout at 450 nm.

The results, shown in Table 3, are the average of duplicate assays and indicate clearly the difference observed in the BSE-affected cattle compared with the healthy cattle.

TABLE 3

| SAMPLE | Average intensity | Coefficient of variation |
| --- | --- | --- |
| Blank (PBS) | 0.172 | 3.6% |
| Healthy CSF | 0.178 | 11.8% |
| Healthy CSF | 0.189 | 2.4% |
| BSE CSF | 0.304 | 1.5% |
| BSE CSF | 0.576 | 4.0% |
| BSE CSF | 0.465 | 10.8% |
| Bovine heart (10 mg/ml.) | 2.872 | 2.0% |
| Blank (PBS) | 0.178 | 2.1% |

Each of the above cited publications is herein incorporated by reference to the extent to which it is relied on herein.

The invention claimed is:

1. A method of identifying a subject suffering from a transmissible spongiform encephalopathy selected from the group consisting of Creutzfeldt-Jakob disease (CJD) and Bovine Spongiform encephalopathy (BSE) in a test subject comprising:

(i) performing an immunoassay for determining a level of brain-derived heart fatty acid binding protein in a body fluid sample derived from said test subject suspected of suffering from a transmissible spongiform encephalopathy selected from the group consisting of CJD and BSE; and (ii) comparing the level of brain-derived heart fatty acid binding protein in the body fluid sample derived from said test subject to the level of brain-derived heart fatty acid binding protein in a body fluid sample derived from a control subject wherein the control subject does not exhibit a transmissible spongiform encephalopathy selected from the group consisting of CJD and BSE;

wherein an elevated level of brain-derived heart fatty acid binding protein in the body fluid sample derived from said test subject compared to the level of brain-derived heart fatty acid binding protein in the body fluid sample derived from the control subject, in combination with clinical evaluation of acute myocardial infarction in the subject and assaying for a marker of acute myocardial infarction in the subject and obtaining a non-elevated level of the marker in comparison with a normal control which is characteristic of the subject having no acute myocardial infarction, identifies that the test subject suffers from the transmissible spongiform encephalopathy selected from the group consisting of CJD and BSE.

2. The method according to claim 1, wherein an antibody to heart fatty acid binding protein is used to determine the level of brain-derived heart fatty acid binding protein.

3. The method according to claim 2, wherein the test subject is a human suffering from CJD and the antibody is a human heart fatty acid binding protein monoclonal antibody.

4. The method according to claim 3, wherein the assay for brain-derived heart fatty acid binding protein comprises a sandwich enzyme linked immunosorbent assay.

5. The method according to claim 2, wherein the assay for brain-derived heart fatty acid binding protein comprises a sandwich enzyme linked immunosorbent assay.

6. The method according to claim 2, wherein the test subject is a bovine subject suffering from BSE and the antibody is an anti rat/mouse FABP monoclonal antibody.

7. The method according to claim 6, wherein the assay for brain-derived heart fatty acid binding protein comprises a sandwich enzyme linked immunosorbent assay.

8. The method according to claim 1, wherein the level of brain-derived heart fatty acid binding protein is measured in a blood plasma or serum sample.

9. The method according to claim 1, wherein the marker of acute myocardial infarction is CK-MB or troponin I.

* * * * *